United States Patent [19]

Gentiluomo

[11] 4,419,881
[45] Dec. 13, 1983

[54] HYDRODYNAMIC PRESSURIZING APPARATUS

[75] Inventor: Joseph A. Gentiluomo, Schenectady, N.Y.

[73] Assignee: The United States of America as represented by the Secretary of the Army, Washington, D.C.

[21] Appl. No.: 374,830

[22] Filed: May 4, 1982

[51] Int. Cl.³ .......................... G01N 3/36; G01M 3/02
[52] U.S. Cl. ............................................ 73/37; 73/167
[58] Field of Search .................. 73/167, 168, 49.4, 37

[56] References Cited

U.S. PATENT DOCUMENTS

| | | | |
|---|---|---|---|
| 3,196,677 | 7/1965 | Day et al. | 73/37 |
| 3,254,524 | 6/1966 | Tannenberg | 73/37 |
| 3,750,459 | 8/1973 | Williams et al. | 73/49.4 |
| 3,955,402 | 5/1976 | Harvill | 73/37 |

Primary Examiner—S. Clement Swisher
Attorney, Agent, or Firm—Robert P. Gibson; Anthony T. Lane; Robert O. Richardson

[57] ABSTRACT

An apparatus capable of stressing test specimens to relatively high stresses at an ultra fast rise time, and unstress at ultra fast decay time. System components include a hydraulic pumping unit, a gas-liquid accumulator, a pressure loading valve, an intensifier, a pressure vessel, a trigger mechanism, a pressure unloading valve, a surge tank, and system controls. To increase system operating response, the discharge port of the accumulator is connected directly to the inlet port of the loading valve. An exit port of the loading valve mounts directly to the inlet low pressure port of the intensifier. The high pressure outlet port of the intensifier mounts directly to the bottom inlet end of the pressure vessel, and the inlet port of the unloading valve mounts directly to a second exit port of the loading valve. The pressure vessel chamber and the intensifier's high pressure chamber are pre-filled as a closed system, with a low compressible fluid. Also, a high speed trigger mechanism in conjunction with the high speed loading valve is used. The trigger mechanism operates to move the trigger valve's spool at high speed for effectuating instant release of fluid pressure behind the loading valve's plunger. The resulting rapid retraction of this plunger will operate to dump pressurized fluid from the accumulator to the low pressure side of the intensifier. Rapid release of fluid pressure from within the pressure vessel is accomplished by operation of the unloading valve in conjunction with the loading valve for effectuating rapid discharge of fluid from the intensifier's low pressure end to the surge tank.

10 Claims, 7 Drawing Figures

HYDRODYNAMIC PRESSURIZING APPARATUS

GOVERNMENT INTEREST

The invention described herein may be manufactured and/or used by or for the Government for governmental purposes without the payment of any royalty thereon.

BACKGROUND OF THE INVENTION

This invention pertains to the field of hydrodynamic pressurization, for subjecting substantially large test specimens to high stresses at high strain rates.

Known prior art includes a hydraulic system using a high pressure liquid accumulator, and a mechanical system in the form of an impact hammer or press, to supply the energy required for the stress testing of specimens. These prior art hydraulic systems subject various size specimens to stresses at substantially low strain rates. They present a hazard due to the use of high pressure liquid accumulators to store the tremendous amount of energy required. The mechanical impact hammer or press systems are noisy, and inherently bulky in order to be able to provide the required rapid high energy output for rapid stressing of large specimens.

SUMMARY OF THE INVENTION

It is often desirable or necessary to evaluate design parameters, study material properties, and determine the operational characteristics of components under simulated service conditions, particularly when the complexity of the component or the service conditions render accurate theoretical solutions impractical or impossible. This invention discloses the design and operation of a high pressure hydrodynamic pressurizing system capable of pressurizing pressure vessels to relatively high pressures at a predetermined ultra fast rise time, and decompress at a predetermined ultra fast decay time. By simulating the pressure-rise and pressure decay curve of cannon chamber pressures, dynamic stress-strain conditions, strength, and low cycle fatigue characteristics of breech rings and tubes can be evaluated without incurring the high expense associated with the actual firing of said cannons for evaluation of said components.

The concept of this invention is embraced within an apparatus consisting basically of a hydraulic pumping unit, a gas-liquid accumulator, a differential pressure loading valve, an intensifier, a pressure vessel, a trigger mechanism, an unloading differential pressure valve, a sure tank, and auxiliary fluid power and electric control equipment. To increase system response, the discharge port of the accumulator is connected directly to the inlet port of the loading valve. The exit port of the loading valve mounts directly to the inlet low pressure port of the intensifier. The high pressure outlet port of the intensifier mounts directly to the bottom inlet end of the pressure vessel, and the inlet port of the unloading valve mounts directly to an exit port of the loading valve. This integral component mounting method is used to increase system response by minimizing fluid flow losses associated with flow path distance, and to minimize the time lag associated with the compression of large volumes of compressible fluids. Also, to improve system response time, the pressure vessel's fluid passageways and the intensifier's high pressure fluid chamber and passageway are pre-filled as a closed system with a low compressible fluid for the purpose of reducing intensifier stroke. The shorter the intensifier stroke, the more affective will be the accumulator in providing the necessary fluid flow rate for ultra-fast pressure build-up within the pressure vessel. Further increase in system response time is attained through use of a high speed trigger mechanism in conjunction with a high speed loading valve. This mechanism operates to move the spool of the trigger valve at high speed for instant release of fluid pressure from behind the plunger of the loading valve. The resulting rapid retraction of said plunger will operate to dump pressurized fluid from the accumulator to the low pressure end of the intensifier. Rapid release of fluid pressure from within the pressure vessel is accomplished by operation of the unloading valve in conjunction with the loading valve, for effectuating rapid discharge of fluid to the surge tank. It is to be discerned that the peak pressure within the pressure vessel can be varied over a wide range of values by simply adjusting the gas charging pressure and the fluid charging pressure within said gas-liquid accumulator. Also, the rate of loading said pressure vessel can be adjusted by varying both the accumulator discharge pressure and the viscosity of the fluid. It is to be noted that the fluid between the accumulator pressure, and the fluid between said loading valve and the low pressure end of the intensifier is always filled with fluid at atmospheric pressure when said intensifier is in the de-energized state.

In general, it is an object of this invention to improve upon the construction and performance of presently available hydrodynamic pressurizing systems. Accordingly, other objects of this invention are as follows:

To provide a hydrodynamic pressurizing system capable of simulating predetermined pressure-time curves for a variety of substantially large test specimens.

To provide a hydrodynamic pressurizing system capable of being used to pressurize a wide variety of pressure vessel configurations at high loading rates.

To provide a hydrodynamic pressurizing system that stores fluid energy at moderate pressure within a gas-liquid type accumulator.

To provide a hydrodynamic pressurizing system whereby safety is substantially increased through the use of a small volume of low compressible fluid within the pressure vessel chamber.

To provide a hydrodynamic pressurizing system using mercury or other low compressible fluid within the pressure vessel and the high pressure side of the intensifier, for improving system response. To provide a hydrodynamic pressurizing system featuring fast operating loading and unloading valves, having built-in cushions for increasing valve life.

To provide a hydrodynamic pressurizing system featuring a digital measuring and display means for indicating pressure vessel fluid pressure.

These objects and other objects of this invention should be discerned and appreciated from the description and claims taken in conjunction with the accompanying drawings in which:

FIG. 5 depicts a schematic representation of the invention. In order to more precisely disclose the invention, U.S.A. Standard Fluid Power Symbols are used for fluid components.

DESCRIPTION OF THE INVENTION

In explaining the invention in detail, it should be discerned that this invention is capable of many embodiments of which the preferred is illustrated in the accompanying drawings and also herein described.

It is to be noted that the herein disclosed hydrodynamic pressurizing apparatus is capable of dynamically pressurizing all types of pressure vessels. One specific application of the invention depicted in the drawings, is to test Breech Assemblies of 105 MM M68 Guns. For testing, the Breech Assemblies are screwed onto the external threaded portion Z of Stub Tube 59, shown in FIG. 1. When Pressure Vessel 46 is pressurized, said Stub Tube 59 will dilate to induce a tensile hoop stress within the Breech Ring, (not shown) and Piston 68 will move axially to bear against and load the Breechblock of the Breech Assembly also not shown.

Figure 1:
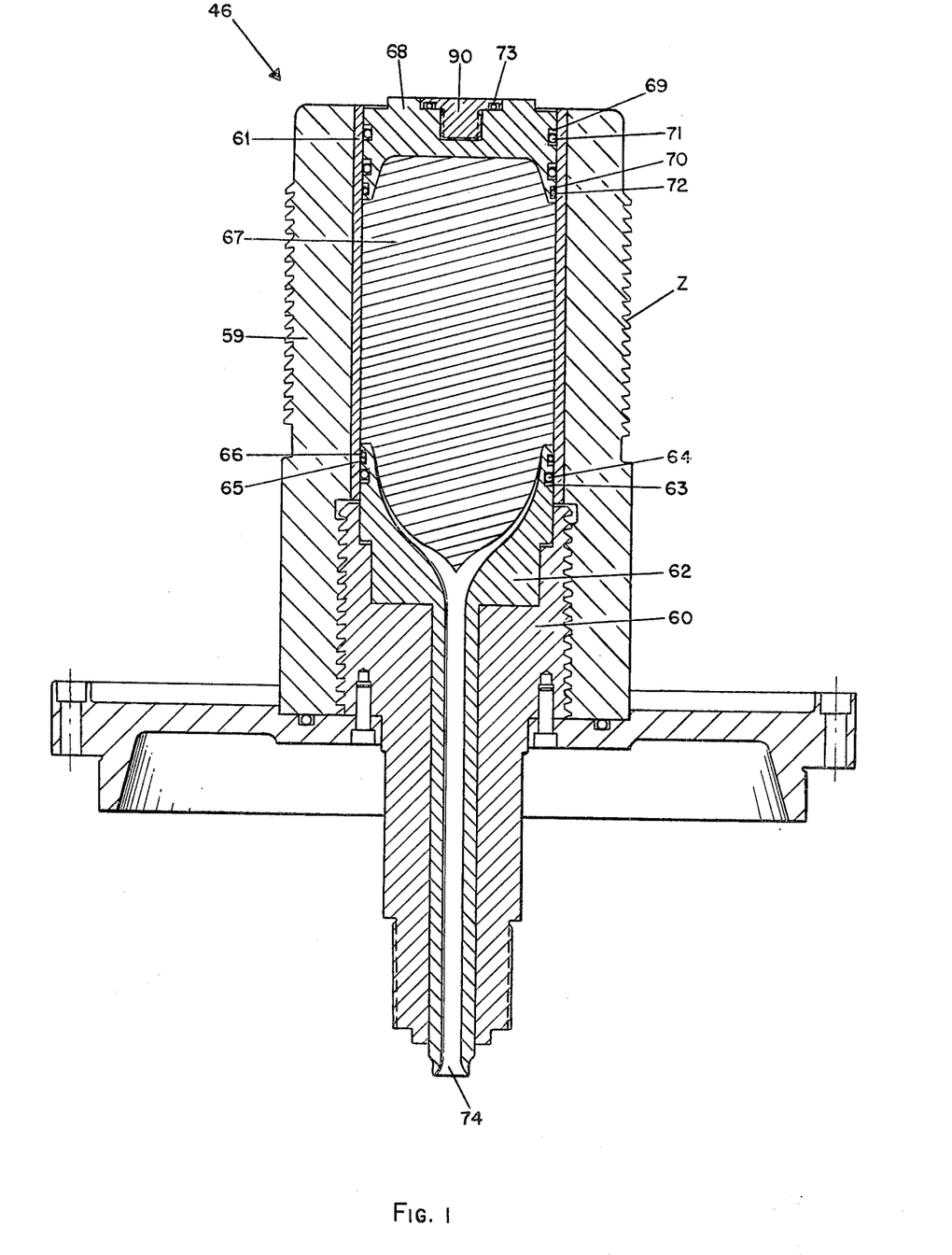
FIG. 1 depicts an elevation view in section of the pressure vessel.
Figure 5:
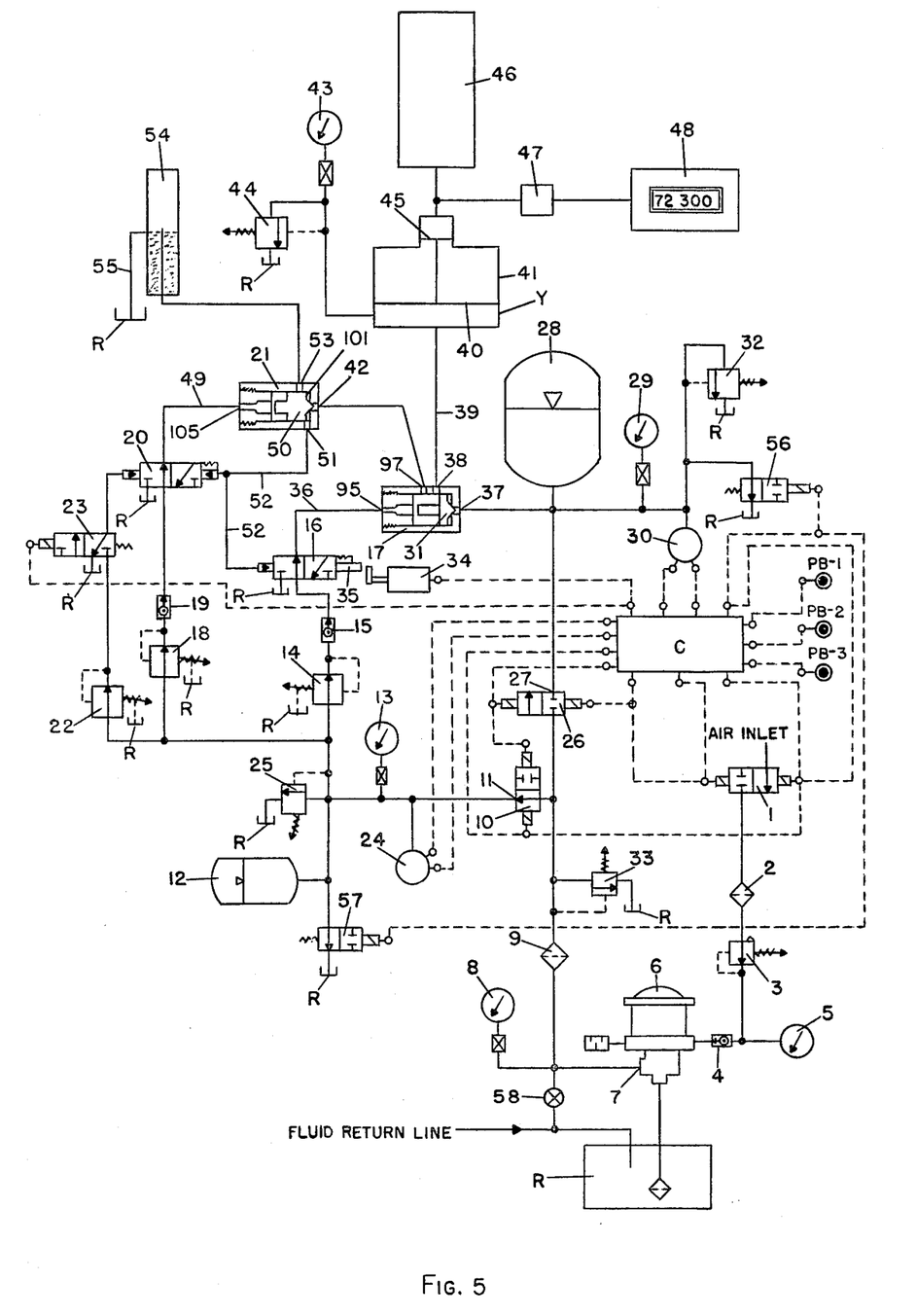

With reference to FIG. 1, it should be noted that Pressure Vessel 46 is made up of Stub Tube 59 having Closure 60 secured to the bottom of the said Stud Tube by means of threads. Stub Tube 59 may have an internal Liner 61 of special material, for protection purposes when the hydraulic fluid used to pressurize the Vessel may have a degrading affect. For example, when a liquid metal such as mercury is used, liquid metal embrittlement may be a problem if the Stub Tube material is not resistant to such attack. This means that all surfaces in contact with mercury that experience tensile stress must be made of special embrittlement resistant material, or otherwise incorporate liners made of a special material such as Liners 61 and 62. Located within Closure Liner 62, are Back-up Rings 63 and 65 assembled in conjunction with O-rings 64 and 66, for preventing fluid leakage. Positioned within the bore of Stub Tube Liner 61, is Filler Bar 67. This Filler Bar is of such size and shape as to accommodate a minimum of fluid within clearances existing between such components as Closure Liner 62, Stub Tube Liner 61, Piston 68, and Filler Bar 67. Piston 68 is reciprocably mounted within Stub Tube Liner 61, and fluid leakage past this Piston is prevented through use of Back-up Rings 69 and 70 in conjunction with O-rings 71 and 72. For bleeding and filling of Pressure Vessel 46, a Bleed Plug 90 is provided. This Plug having O-ring 73, is centrally mounted and secured within the Piston by means of threads. When fluid pressure from Intensifier 41, in FIG. 5, is conveyed into Passage 74 of Closure 60, the Stub Tube 59 will dilate radially to impress a tensile hoop stress to the Breech Ring mounted thereupon, but now shown in FIG. 1. Also, Piston 68 will move axially against the Breechblock (not shown) to impose an additional stress to the rear end of the Breech Ring (also not shown).

Figure 2:
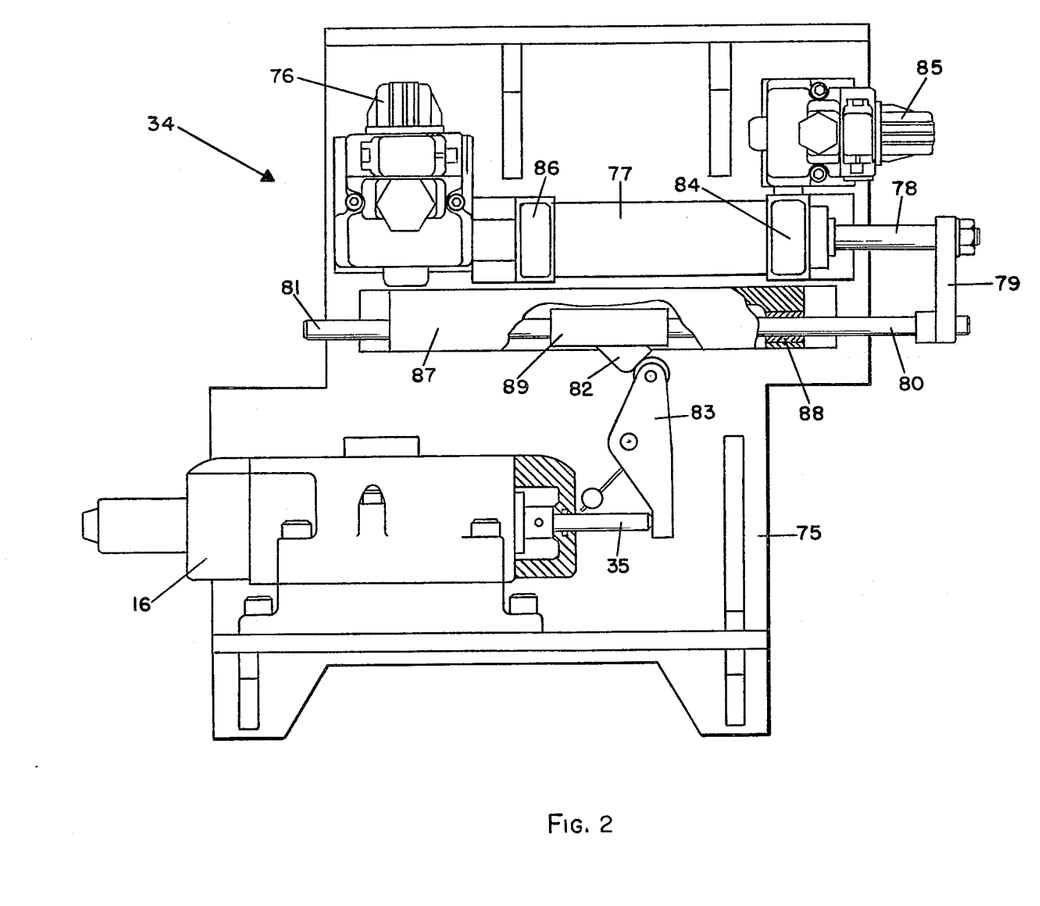
FIG. 2 depicts the trigger mechanism.

Trigger Mechanism 34 depicted in FIG. 2 consists of Mounting Structure 75 having Trigger Valve 16, Support 87, Cylinder 77, and Air Valves 76 and 85 fixedly mounted thereto. Guide Rods 80 and 81 are fixedly mounted to Holder 89, and also slidably mounted within Bearings 88 which in turn are fixedly mounted within both ends of Support 87. Limit Switch Actuators 84 and 86 are fixedly mounted to both ends of Cylinder 77 as shown. Cylinder Rod 78 is rigidly interconnected to Guide Rod 80 through means of Tie Bar 79 and appropriate fasteners. Actuating Cam 82 is fixedly mounted into Holder 89, and positioned such as to actuate Interposer Lever 83. Lever 83 is pivotly mounted to said Mounting Structure 75 and positioned such as to contact Spool 35. Actuating Cam 82 protrudes from said Holder 89 a preset distance such as to impose proper movement to said Lever 83. The disclosed Trigger Mechanism is used to initiate system pressurization for attaining ultra fast peak pressure rise times during pressurization of the Pressure Vessel 46 shown in FIG. 1.

When PB-2 is depressed, Valve 76 in FIG. 2 is actuated such as to convey air to Cylinder 77, to drive Rod 78 forward (to the right in FIG. 2). Rod 78, through Tie Bar 79, will drive the assembly consisting of Holder 89, Actuating Cam 82, and Guide Rods 80 and 81 at high speed. Actuating Cam 82 will in turn trip Interposer Lever 83 such that Spool 35 of Trigger Valve 16 will be so positioned as to effectuate the dumping of fluid from Valve 17, in FIG. 5, to the Reservoir by way of Pipe Line 36. When Rod 78, in FIG. 2, reaches its extreme extended position (to the right in FIG. 2), Limit Switch Actuator 84 will be actuated to provide a signal to the System Electrical Controls C, in FIG. 5, which will in turn operate to de-energize Air Valve 76 and energize Air Valve 85, in FIG. 2. In so doing, air is conveyed to the head end of Cylinder 77 to drive it back to its starting position (to the left in FIG. 2). At this position, Limit Switch Actuator 86 will be actuated to de-energize Air Valve 85 and place Trigger Mechanism 34 in the ready condition for subsequent operation.

Figure 3:
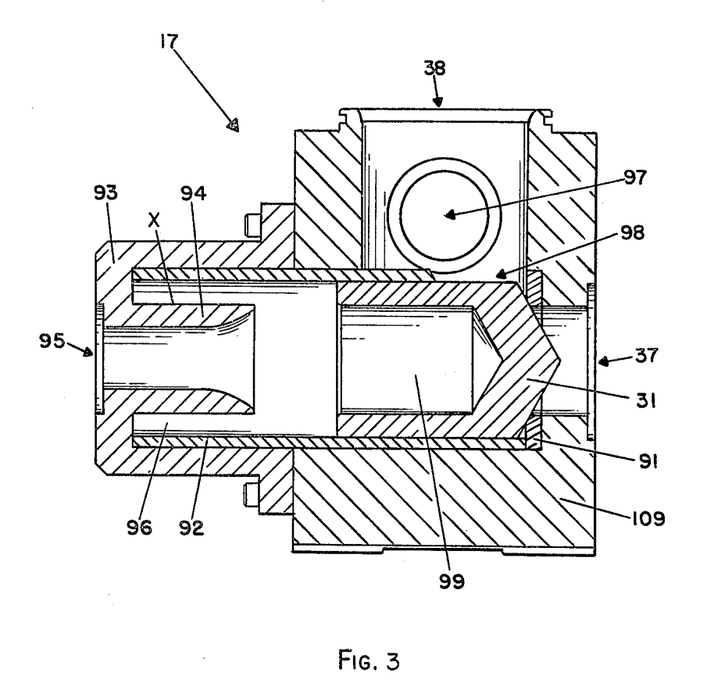
FIG. 3 depicts in section the loading differential pressure valve.

FIG. 3 depicts the Loading Differential Pressure Valve 17 which is of the high speed type for the purpose of improving response time for initiating system pressurization. This valve is used to direct the flow of high energy fluid from Accumulator 28, in FIG. 5, to Intensifier 41, in FIG. 5. Valve 17 is designed on the differential area principle, and structured to provide minimal fluid friction losses. It is to be noted that this Valve has an Inlet Port 37, two Exit Ports 38 and 97, and a Cushion Port 95. Valve Body 109 has Seat 91 mounted within it adjacent to Inlet Port 37. This Seat 91 is held in position by Liner 92 which is pushed against the Seat when Cap 93 is fixedly mounted to Valve Body 109 by suitable fastening means. Liner 92 has Liner Opening 98 in alignment with Exit Port 38. Plunger 31 is slidably mounted within Liner 92 such that when positioned under fluid pressure against Seat 91, will operate to seal off Inlet Port 37. Cap 93 contains Cushion 94 having a diameter of such size as to allow Plunger Cavity 99, of Plunger 31, to pass thereonover with slight clearance therebetween. In operation, fluid of predetermined pressure is introduced through Cushion Port 95 into the Valve chamber behind Plunger 31 to hold the cone end of the Plunger against Seat 91 for sealing off Inlet Port 37. When fluid is to be conveyed from Inlet Port 37 to Exit Ports 38 and 97, the pressurized fluid acting behind Plunger 31 must be released through Port 95. When fluid is dumped from Port 95, moderately high pressure fluid from within Accumulator 28, in FIG. 5, enters through Port 37 to displace Plunger 31 from its seat 91 at high speed. As Plunger 31 moves away from its seat, fluid from Port 37 is forced through Liner Opening 98 for conveyance to Exit Ports 38 and 97. To absorb the Plunger's kinetic energy during retraction, a decelerating cushioning arrangement is used. Cushioning is effectuated after Plunger 31 is sufficiently displaced to expose Liner Opening 98. As Plunger 31 continues movement away from its Seat 91, Cushion 94 will engage and enter Plunger Cavity 99 to trap fluid within Annular Space 96. Since a small clearance exists between Plunger Cavity 99 and the Cushion's diametral surface, trapped fluid within Annular Space 96 will bleed out slowly through Cushion Port 95 to effectuate Plunger deceleration.

Figure 4:
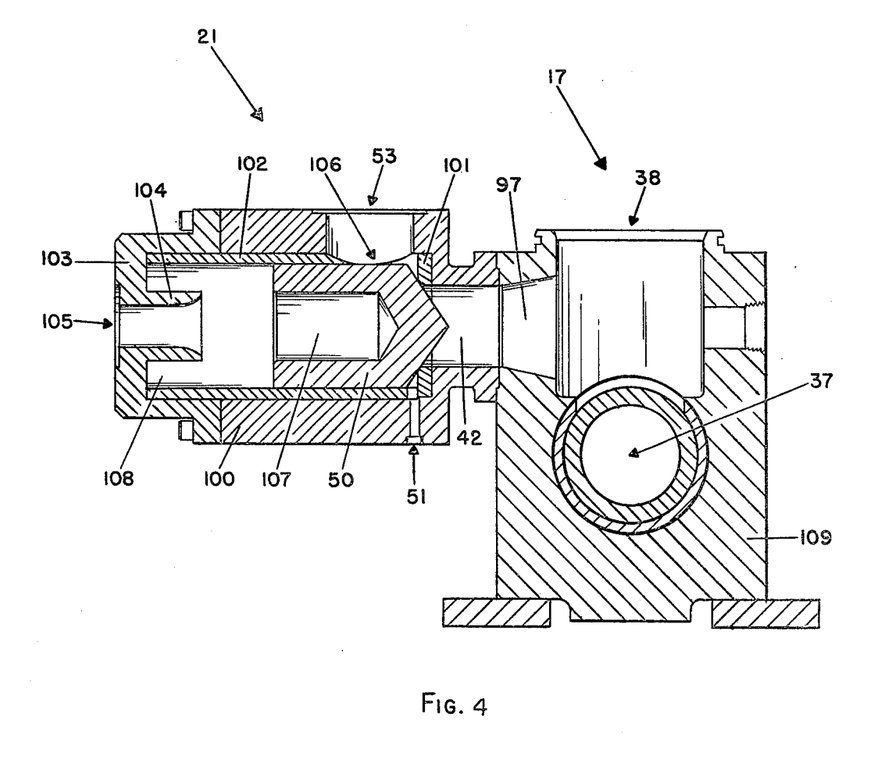
FIG. 4 depicts in section the unloading differential pressure valve fixedly mounted to an exit port of the loading differential pressure valve.

FIG. 4 depicts the Unloading Differential Pressure Valve 21, directly attached to Port 97 of Loading Differential Pressure Valve 17. This Unloading Valve functions to relieve Intensifier fluid pressure at a preset value, by dumping fluid to the Reservoir R, in FIG. 5, after a specific time and at a preset rate. The construction of Valve 21 includes Valve Body 100 having Inlet Port 42, Exit Port 53, Pilot Port 51, and Cushion Port 105. Seat 101 is mounted within Body 100 adjacent to Inlet Port 42. Seat 101 is held in position by Liner 102 which is pushed against Seat 101 when Cap 103 is fixedly mounted to said Valve Body 100 by suitable fastening means. Liner 102 has Liner Opening 106 opposite Exit Port 53, and also an opening opposite Pilot Port 51. Plunger 50 is slidably mounted within Liner 102 such that when positioned under fluid pressure against Seat 101, it will operate to seal off Inlet Port 42. Cap 103 contains Cushion 104 having a diameter of such size as to allow Plunger Cavity 107, of Plunger 50, to pass thereonover with slight clearance therebetween. In operation, fluid of predetermined pressure is introduced through Cushion Port 105 into the valve chamber behind Plunger 50, to hold the cone end of Plunger 50 against Seat 101 for sealing off Inlet Port 42. When fluid pressure acting on the low pressure side Y of Intensifier 41, in FIG. 5, exceeds the preset pressure acting within the valve chamber behind Plunger 50, the Plunger will be displaced from its seat 101. In so doing, pressurized fluid will be discharged through Pilot Port 51 to shift the spool of Valve 20 in FIG. 5. Valve 20 will then operate to dump, by way of Port 105, the fluid acting against Plunger 50. Immediately, fluid pressure within the low pressure side Y of Intensifier 41 in FIG. 5 will act to further displace Plunger 50 away from Seat 101. During this Plunger movement, fluid from Port 42 will be forced through Liner Opening 106 for conveyance through Exit Port 53. To absorb the Plunger's kinetic energy during retraction, a decelerating cushioning arrangement is used similar to that used in Valve 17. Cushioning is effectuated after Plunger 50 is sufficiently displaced to expose Liner Opening 106. As the Plunger continues movement away from its Seat, Cushion 104 will engage and enter Plunger Cavity 107 to trap fluid within Annular Space 108. Since a small clearance exists between the Plunger Cavity and the Cushion's diametral surface, trapped fluid within Annular Space 108 will bleed out slowly through Cushion Port 105 to effectuate Plunger deceleration.

Figure 6A:
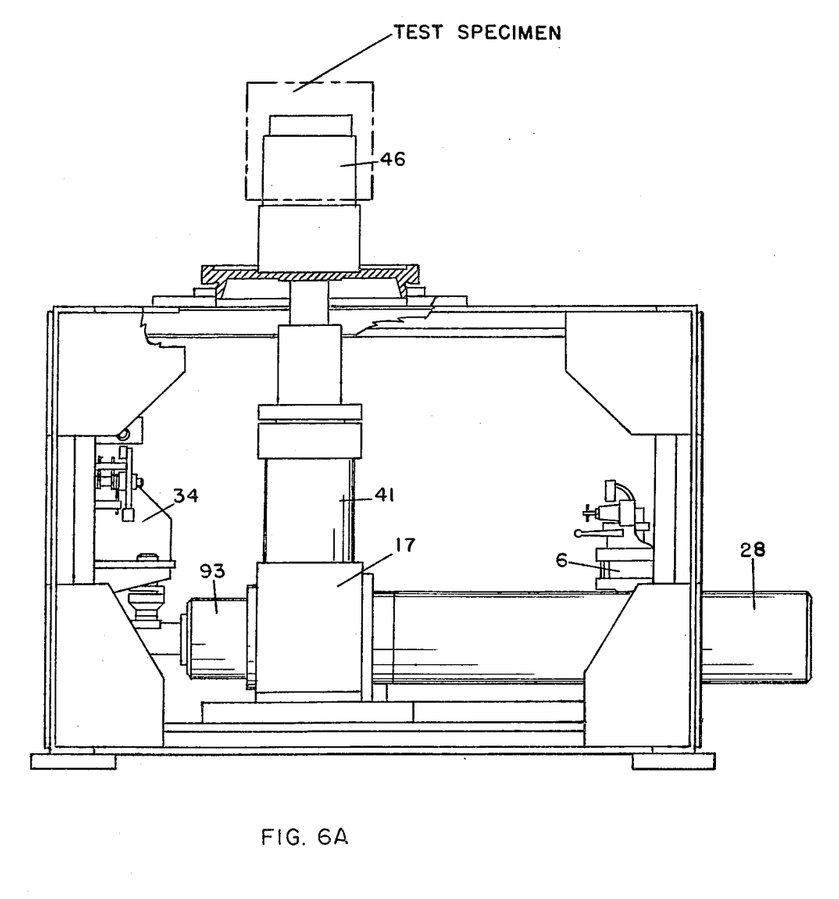
FIGS. 6A and 6B depict elevation views of the invention.
Figure 6B:
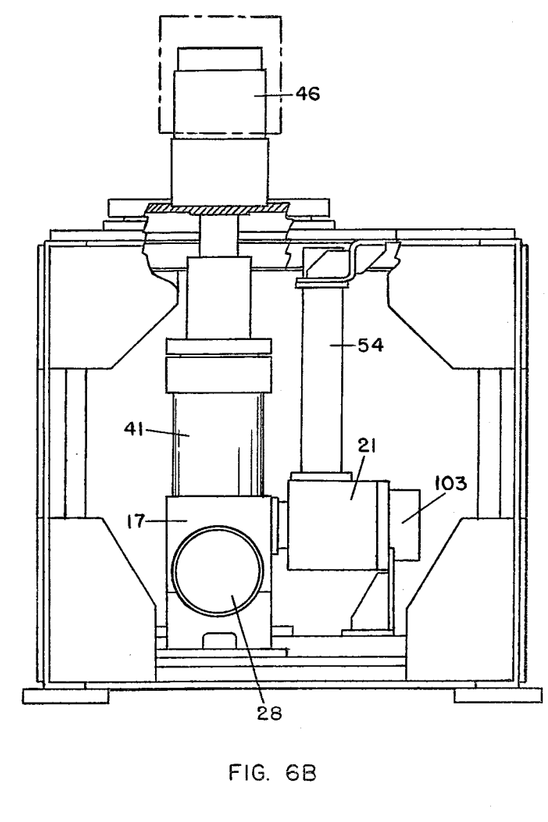

It should be noted that Loading Valve 17, in FIG. 5, are specially manufactured components. Also, Accumulator 28 and Intensifier 41, in FIG. 5, are modified commercially available items. All of these items must be either manufactured or modified such as to have the capability of being directly mounted to each other as depicted in FIGS. 6A and 6B. With reference to FIG. 5, it should be noted that Auxiliary Fluid Power Equipment encompasses all depicted fluid power items, with the exclusion of Surge Tank 54, Intensifier 41, Accumulator 28, Loading Valve 17, Unloading Valve 21, and Trigger Valve 16. U.S.A. Standard Fluid Power Symbols are used for fluid components in the FIG. 2 schematic representation of the invention. Also, the Auxiliary Electric Control Equipment encompasses all depicted electric control items with the exception of Controls C. It should be further noted that all Auxiliary Fluid Power and Electric Control Equipment disclosed herein, are commercially available items except for those noted above.

The overall operation of the herein disclosed system is described for one cycle of operation as follows: (Refer to FIG. 52)

When System Start Push Button PB-1 is depressed, Bleed-Down Valves 56 and 57 will be energized to the closed position, and Valve 1 will be actuated such as to allow pressurized air to pass through Air Filter 2, Pressure Regulator 3, and Speed Control Valve 4 to air driven Hydraulic Pump 6. Input air pressure to Pump 6 is displayed on Pressure Gage 5. Input air is adjusted such as to control and set the magnitude of the Pump's output pressure. Also, the pumping rate of Pump 6 is set through adjustment of Speed Control Valve 4. It should be noted that air driven liquid Pump 6 is of the commercially available type which utilizes a large area piston at low pressure to produce a substantially high hydraulic pressure on a small area hydraulic piston. Hydraulic fluid at atmospheric pressure is drawn from Reservoir R and discharge at intensified pressure through the Pump's Output Port 7. Pressurized fluid emitted from Port 7 has its pressure reading displayed on Pressure Gage 8 while fluid is pumped through Filter 9 and Port 11 of Valve 10, onward to Gas-Liquid Accumulator 12. As fluid pressure builds up within Accumulator 12, its pressure reading is displayed on Pressure Gage 13. When fluid pressure within Accumulator 12 reaches the high level limit preset in Pressure Switch 24, this Switch will operate in conjunction with System Control C to actuate Valve 10 such as to terminate flow therethrough. Accumulator 12 will then operate to maintain a controlled preset fluid pressure to Valves 17, 21 and 23 through pressure regulation provided by Pressure Reducing Valves 14, 18 and 22. Pressure Relief Valve 25 is used as a safety means to assure that pressure within the Accumulator's hydraulic circuit does not accidentally exceed the value preset on Pressure Switch 24. It should be noted that when Pressure Switch 24 is operated in conjunction with System Controls C to effectuate closing of Valve 10, Valve 26 will be simultaneously opened to provide pressurized fluid through Port 27 to said Gas-Liquid Accumulator 28. As pressure builds up within the circuit of Accumulator 28, fluid pressure readings will be displayed on Pressure Gage 29. Also, Accumulator circuit pressure will act on Pressure Switch 30 and Plunger 31 of Loading Differential Pressure Valve 17. When pressure within Pressure Switch 30 reaches the preset high level limit, the Switch in conjunction with System Controls C will operate to actuate Valve 1 to its normally closed position to terminate operation of Pump 6. Also, Valve 26 will be simultaneously actuated to the normally closed position to cut off pressurized fluid to Accumulator 28. Pressure Relief Valve 32 is used as a safety means to assure that pressure within the Accumulator's hydraulic circuit does not accidentally exceed the valve preset on Pressure Switch 30. Also, Pressure Relief Valve 33 is used as a safety means to protect Pump 6 and the remainder of its fluid circuit in the event Pressure Switch 30 and Relief Valve 32 fail to function properly during pressurization of Accumulator 28.

It should be noted that during system operation, fluid from Accumulator 12 is conveyed through Pressure Reducing Valve 14, Flow Control Valve 15, and Valve 16, to Valve 17 by way of Pipe Line 36. Pressurized fluid from Accumulator 12 is simultaneously conveyed through Pressure Reducing Valve 18, Flow Control Valve 19, and Valve 20 to provide fluid to Unloading Differential Pressure Valve 21 by way of Pipe Line 49. Also, Accumulator 12 supplies fluid through Pressure Reducing Valve 23.

To initiate the dynamic pressurizing cycle, PB-2 is depressed to actuate Trigger Mechanism 34 and Valve 23. During actuation, Trigger Mechanism 34 will provide a displacement to Spool 35 of Trigger Valve 16. Also, Valve 23 will be pulsed to admit fluid momentarily to Valve 20 to shift its spool. In so doing, Valve 20 will provide pressurized fluid to Valve 21 such as to hold Plunger 50 against its Seat 101. Simultaneously, Valve 16 will terminate fluid pressure to Loading Differential Pressure Valve 17, and in turn divert and dump the Pressurized fluid through Pipe Line 36 to the Reservoir R of Valve 16. As this fluid is dumped, pressurized fluid from within Accumulator 28 will act against and displace Plunger 31 such as to admit fluid to Inlet Port 37. Opening of Port 37 will allow fluid to be diverted through Port 38 into Passage 39 for conveyance to the Intensifier's 41 low pressure side, and to Inlet Port 42 of Unloading Differential Pressure Valve 21. The pressure within the Intensifier's low pressure chamber Y is displayed on Pressure Gage 43, and monitored by Pressure Relief Valve 44. Should the pressure exceed the pre-set value, Valve 44 will operate to dump fluid to the Reservoir, thereby protecting the system from overpressurization. During pressure build-up within the low pressure chamber of said Intensifier 41, Piston 40 will rise to effectuate the intensification of fluid pressure within the small chamber above Piston 45. This intensified fluid pressure is in turn conveyed to Pressure Vessel 46 and Pressure Transducer 47. The pressure sensed by Transducer 47 will be displayed on the commercially available Digital Pressure Readout Unit 48. It is to be discerned that the fluid pressure in Pipe Line 49 is such as to allow Plunger 50 of Valve 21 to retract from its Seat 101 when the pressurized fluid underneath Piston 40 attains a predetermined set value. Upon movement of Plunger 50, fluid will enter Port 42 and discharge through Pilot Port 51 into Pipe Lines 52. Further movement of Plunger 50 will allow fluid to be discharged through Port 53 into Surge Tank 54. As the level of fluid within Surge Tank 54 reaches a predetermined height, additional fluid will be discharged through the Over-flow Line 55 into its Reservoir R. It is to be noted that Surge Tank 54 is elevated to such a position as to always maintain fluid between Exit Port 38, Inlet Port 42, and the Intensifier's low pressure chamber Y. Upon discharge of said fluid into Pipe Lines 52, Spools of both Valves 16 and 20 will be shifted in position. In so doing, Valve 16 will allow the conveyance of fluid through Pipe Line 36 to move Plunger 31 to seal off Inlet Port 37 of Valve 17. With no fluid passing through Port 38, pressurized fluid will be cut off to Intensifier 41 during the period of fluid discharge through Valve 21. The pressurized fluid entering Valve 20 by way of Pipe Line 52, will position the Spool of Valve 20 such as to dump fluid through Port 105 of Valve 21, to Reservoir R of Valve 20 by way of Pipe Line 49. This action will allow Plunger 50 to be further displaced from Seat 101 to allow for instant decompression of Intensifier 41. When fluid pressure within Accumulator 28 drops to the predetermined preset low level limit, Pressure Switch 30 in conjunction with System Control C will automatically operate Valve 1 to once again provide pressurized air for operation of Pump 6. Also, Valve 10 will be actuated to admit fluid to Accumulator 12 until Pressure Switch 24 reaches the high level limit. Switch 24 in conjunction with System Control C will then immediately operate to terminate flow through Valve 10 and commence flow through Valve 26 for charging of Accumulator 28. This automatic mode of operation for charging Accumulators 12 and 28 will be the same as previously described for initiation of system operation through depressing of PB-1.

It is to be also discerned that should pressure within Accumulator 12 drop below the preset low level limit set on Pressure Switch 24, this Pressure Switch in conjunction with System Controls C will automatically operate to actuate Valve 1 to its open position for operation of Pump 6. Simultaneously, Valve 10 will be actuated to admit pressurized fluid to Accumulator 12 until Pressure Switch 24 reaches the high level limit. Switch 24 in conjunction with said System Controls C will then again operate to terminate flow through Valve 10, and commence flow through Valve 26 to Accumulator 28 until the pressure within Accumulator 28 reaches the high level limit set on Pressure Switch 30. When this occurs, Pump 6 will be deactivated as previously disclosed.

When the aystem is to be shut down, System Stop push button PB-3 is depressed. In so doing, Valve 1 will revert to its normally closed position, thereby terminating operation of Pump 6. Also, as a safety measure, Bleed-Down Valves 56 and 57 will be de-energized to return these Valves to their normally open position. With Valves 56 and 57 in open position, pressurized fluid within Accumulators 12 and 28 will be discharged to Reservoir R. When required, Pressure Release Valve 58 is used to relieve pressure and drain fluid from within the Pipe Lines connected between Pump 6, and Valves 10 and 26.

Having thusly described the invention, the following is claimed:

1. A Hydrodynamic Pressurizing Apparatus comprising:
   (a) a loading valve having a cushion port, an inlet port, and a first and second exit port,
   (b) an accumulator having a discharge port mounted directly to said inlet port of said loading valve;
   (c) an intensifier having a low pressure port mounted directly to said first exit port of said loading valve; said intensifier having a high pressure outlet port;
   (d) an unloading valve having an inlet port mounted directly to said second exit port of said loading valve; said unloading valve having an exit port,
   (e) a pressure vessel having a bottom inlet and mounted directly to said high pressure outlet port of said intensifier;
   (f) and auxiliary fluid power and electric control equipment functionally associated with said loading valve, said accumulator, said intensifier, said unloading valve, and said pressure vessel, to provide proper system operation.

2. The invention as defined in claim 1, further characterized as including a surge tank having an entrance port mounted directly to said exit port of said unloading valve.

3. The invention as defined in claim 2, further characterized as including a trigger mechanism having the trigger valve's exit port connected to said cushion port of said loading valve.

4. The invention as defined in claim 3, wherein said auxiliary fluid power equipment is further characterized as including a hydraulic pumping unit having its fluid output line connected such as to provide pressurized fluid to said accumulator's discharge port.

5. The invention as defined in claim 4, wherein said loading and unloading valves having slidably mounted plungers, are further characterized as including built-in cushions to effectuate plunger deceleration.

6. The invention as defined in claim 5, wherein said auxiliary fluid power and electric control equipment are further characterized as including a pressure transducer connected between said intensifier and said pressure vessel, and a digital pressure readout unit electrically connected to said pressure transducer for displaying pressure existing within said pressure vessel.

7. The invention as defined in claim 6, wherein said pressure vessel is further characterized as consisting of a stub tube having an axially movable piston at one end, a fixedly mounted closure at the other end, and a filler bar loosely fitted within said stub tube and intermediate said piston and said closure.

8. The invention as defined in claim 7, wherein said closure is further characterized as having an upper section with a specially contoured concave surface, and said filler bar is further characterized as having a specially contoured nose portion adjacent said closure's contoured surface for purpose of reducing fluid friction and turbulence between said contoured surfaces.

9. The invention as defined in claim 8, further characterized as containing low compressible fluid within said pressure vessel and said intensifier's high pressure section.

10. The invention as defined in claim 9, wherein said low compressible fluid is further characterized as being mercury.

* * * * *